(12) United States Patent
Keusenkothen et al.

(10) Patent No.: US 9,790,145 B2
(45) Date of Patent: *Oct. 17, 2017

(54) PRODUCTION OF $C_{2+}$ OLEFINS

(71) Applicant: ExxonMobil Chemical Patents Inc., Baytown, TX (US)

(72) Inventors: Paul F. Keusenkothen, Houston, TX (US); Juan D. Henao, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 244 days.

This patent is subject to a terminal disclaimer.

(21) Appl. No.: 14/543,365

(22) Filed: Nov. 17, 2014

(65) Prior Publication Data
US 2015/0158791 A1 Jun. 11, 2015

Related U.S. Application Data

(60) Provisional application No. 61/912,886, filed on Dec. 6, 2013.

(30) Foreign Application Priority Data

Feb. 5, 2014 (EP) .................... 14153944

(51) Int. Cl.
*C07C 2/76* (2006.01)
*C07C 2/86* (2006.01)
*C08F 10/00* (2006.01)
*C07C 1/06* (2006.01)
*C07C 5/333* (2006.01)

(52) U.S. Cl.
CPC ............. *C07C 2/864* (2013.01); *C07C 1/06* (2013.01); *C07C 2/76* (2013.01); *C07C 2/862* (2013.01); *C07C 5/333* (2013.01); *C08F 10/00* (2013.01); *C07C 2529/06* (2013.01); *C07C 2529/65* (2013.01); *C07C 2529/70* (2013.01); *C07C 2529/85* (2013.01)

(58) Field of Classification Search
CPC .. C07C 1/06; C07C 5/333; C07C 2/76; C07C 2/864; C07C 2/862; C07C 11/04; C07C 11/06; C07C 5/33; C08F 10/00
See application file for complete search history.

(56) References Cited

U.S. PATENT DOCUMENTS

| | | | |
|---|---|---|---|
| 3,700,585 A | 10/1972 | Chen et al. | |
| 3,702,886 A | 11/1972 | Argauer et al. | |
| 3,709,979 A | 1/1973 | Chu et al. | |
| 3,832,449 A | 8/1974 | Rosinski et al. | |
| 3,911,041 A | 10/1975 | Kaeding et al. | |
| 3,928,483 A | 12/1975 | Chang et al. | |
| 3,931,349 A | 1/1976 | Kuo | |
| 4,016,218 A | 4/1977 | Haag et al. | |
| 4,016,245 A | 4/1977 | Plank et al. | |
| 4,046,825 A | 9/1977 | Owen et al. | |
| 4,049,573 A | 9/1977 | Kaeding | |
| 4,062,905 A | 12/1977 | Chang et al. | |
| 4,076,842 A | 2/1978 | Plank et al. | |
| 4,079,095 A | 3/1978 | Givens et al. | |
| 4,079,096 A | 3/1978 | Givens et al. | |
| 4,088,706 A | 5/1978 | Kaeding | |
| 4,111,847 A | 9/1978 | Stiles | |
| 4,138,440 A | 2/1979 | Chang et al. | |
| RE29,948 E | 3/1979 | Dwyer et al. | |
| 4,175,169 A * | 11/1979 | Beals ............... | B01J 19/242 526/352.2 |
| 4,229,424 A | 10/1980 | Kokotailo | |
| 4,234,231 A | 11/1980 | Yan | |
| 4,439,409 A | 3/1984 | Puppe et al. | |
| 4,440,871 A | 4/1984 | Lok et al. | |
| 4,499,327 A | 2/1985 | Kaiser | |
| 4,556,477 A | 12/1985 | Dwyer | |
| 4,826,667 A | 5/1989 | Zones et al. | |
| 4,873,067 A | 10/1989 | Valyocsik et al. | |
| 4,954,325 A | 9/1990 | Rubin et al. | |
| 5,227,555 A * | 7/1993 | Rhoe ............... | C10G 59/02 208/135 |
| 5,236,575 A | 8/1993 | Bennett et al. | |
| 5,250,277 A | 10/1993 | Kresge et al. | |
| 5,336,825 A | 8/1994 | Choudhary et al. | |
| 5,362,697 A | 11/1994 | Fung et al. | |
| 5,370,851 A | 12/1994 | Wilson | |
| 5,633,417 A | 5/1997 | Beck et al. | |

(Continued)

FOREIGN PATENT DOCUMENTS

| | | |
|---|---|---|
| CN | 101244969 | 8/2008 |
| EP | 0293032 | 7/1993 |
| EP | 1704132 | 7/2005 |
| EP | 2184269 | 5/2010 |
| GB | 2191212 | 12/1987 |
| WO | 97/17290 | 5/1997 |
| WO | 2004/087624 | 10/2004 |
| WO | 2012/099674 | 7/2012 |

OTHER PUBLICATIONS

Baerlocher (Atlas of Zeolite Framework Types, 5th ed. 2001, p. 10-14).*
Chemical and Engineering News, 63(5), 27 (1985).
Chemistry Letters, 35 (2), 142-147, 2006.
Catalysis Letters, 28, 241-248 (1994).
G. Centi, G. Cum, J.L.G. Fierro and J. M. Lopez Nieto, "Direct Conversion of Methane, Ethane, and Carbon Dioxide to Fuels and Chemicals", The Catalyst Group Resources Inc., Spring House, 2008.

(Continued)

*Primary Examiner* — In Suk Bullock
*Assistant Examiner* — Jason Chong

(57) ABSTRACT

This disclosure relates to the production of $C_{2+}$ olefins from feeds containing methane and at least one co-reactant, to equipment and materials useful in such processes, and to the use of such olefins in, for example, the production of polymers.

19 Claims, No Drawings

(56) References Cited

U.S. PATENT DOCUMENTS

| | | | |
|---|---|---|---|
| 5,675,047 A | 10/1997 | Beck et al. | |
| 5,936,135 A | 8/1999 | Choudhary et al. | |
| 6,077,498 A | 6/2000 | Diaz Cabanas et al. | |
| 6,121,504 A * | 9/2000 | Kuechler | C07C 1/20 585/638 |
| 6,200,536 B1 | 3/2001 | Tonkovich et al. | |
| 6,219,973 B1 | 4/2001 | Lafferty | |
| 6,365,792 B1 | 4/2002 | Stapf et al. | |
| 6,518,475 B2 | 2/2003 | Fung et al. | |
| 6,756,030 B1 | 6/2004 | Rohde et al. | |
| 7,008,610 B2 * | 3/2006 | Cao | B01J 29/70 423/706 |
| 7,014,807 B2 | 3/2006 | O'Brien | |
| 7,015,369 B2 | 3/2006 | Hack et al. | |
| 7,022,888 B2 | 4/2006 | Choudhary et al. | |
| 7,453,018 B2 | 11/2008 | Dakka et al. | |
| 7,659,437 B2 * | 2/2010 | Iaccino | C07C 2/78 585/400 |
| 7,799,962 B2 | 9/2010 | Dakka et al. | |
| 7,977,519 B2 | 7/2011 | Iaccino et al. | |
| 8,119,076 B2 | 2/2012 | Keusenkothen et al. | |
| 8,138,384 B2 | 3/2012 | Iaccino et al. | |
| 8,552,247 B2 | 10/2013 | Noe et al. | |
| 2005/0010748 A1 | 1/2005 | Osborn | |
| 2006/0149109 A1 | 7/2006 | Ruziska et al. | |
| 2007/0161717 A1 | 7/2007 | Hu et al. | |
| 2007/0259972 A1 | 11/2007 | Lattner et al. | |
| 2008/0033218 A1 | 2/2008 | Lattner et al. | |
| 2012/0083637 A1 | 4/2012 | Clem et al. | |

OTHER PUBLICATIONS

R.M. Navarro, M.A. Pena and J.L.G.Fierro, Chem. Rev., vol. 107, p. 3952, 2007.

V.R. Choudhary, A.K.Kinage and T.V.Choudhary, Science, vol. 275, pp. 1286-1288, 1997.

V.R. Choudhary and P. Devadas, Microporous and Mesoporous Materials, vol. 23, pp. 231-238, 1998.

J. Guo, H. Lou, H. Zhao, L.Zheng and X.Zheng, Journal of Molecular Catalysis A: Chemical, vol. 239, pp. 222-227, 2005.

J. Gou, H. Lou and X. Zheng, Journal of Natural Gas Chemistry, vol. 18, pp. 260-272, 2009.

O.A. Anunziata, G. A. Eimer and L.B.Pierella, Applied Catalysis A: General, vol. 190, pp. 169-176, 2000.

Alkhawaldeh Ammar et al.: "Conversion of mixtures of methane and ethylene or acetylene into liquids", Pre-Print Archive—Amer. Inst. of Chem Engr., Spring National Meeting, New Orleans, LA USA, Mar. 11-14, 2001 Proceedings of the Second Topical Conference on Natural Gas Utilization, American Institute of Chemical Engineer, Jan. 1, 2002(Jan. 1, 2002) p. 416 paragraph 3; figure 4.

X1Ao-Song Li et al; "A process for a high yield of aromatics from the oxygen-free conversion of methane: combining plasma with Ni/HZSM-5 catalysts", Green Chemistry, vol. 9, No. 6, Jan. 1, 2007 (Jan. 1, 2007), p. 647, col. 2, last paragraph p. 650, col. 2, paragraph 1: figures 1-3.

V Ha: "Aromatization of methane over zeolite supported molybdenum: active sites and reaction mechanism", Journal of Molecular Catalysis A: Chemical, vol. 181, No. 1-2, Mar. 25, 2002, pp. 283-290.

Oscar A. Anunziata: Catalysis Letters, vol. 87, No. ¾, Jan. 1, 2003, 167-171.

"Conversion of biomass-derived syngas to alcohols and C2 oxygenates using supported Rh catalysts in a microchannel reactor", Jiami Hu, Yong Wang, Chusha Cao, Douglas C. Elliot, Don J. Stevens, James F. White, 1, Jan. 30, 2007, Catalysis Today vol. 120, pp. 90-95.

H. Yagita et al., Environmental Catalysis, G. Centi et al. Eds. SCI Publicaiton, Rome, 1995, pp. 639-642.

"Iron Particle Size Effects for Direct Production of Lower Olefins for Synthesis Gas", Hirsa M. Torres Galvis, Johannes H. Bitter, Thomas Davidian, Matthijs Ruitenbeek, A. Iulian Dugulan, and Krijn P. de Jong.s.1 : Journal of American Chemical Society, Sep. 6, 2012, Journal of the American Chemical Society.

"Supported Iron Nanoparticles as Catalysts for Sustainable Production of Lower Olefins", Hirsa M. Torres Galvis, Johannes H. Bitter, Chaitanya B. Khare, Matthijs Ruitenbeak, A. Luian Dugulan, and Krijn P. de Jong, 335, Feb. 17, 2012, Science, vol. 6070, pp. 835-838.

"Heterogeneous Catalytic Synthesis of Ethanol from Biomass-Derived Syngas", James J. Spivey, Adefemi Egbebi, Mar. 7, 2007, Chemical Society Reviews, vol. 38, pp. 1514-1515.

"Ruthenium Melt Catalysis", Producing Chemicals from Synthetic Gas, Knifton, John F. 2, Austin, Texas s.n., 1985, vol. 29, p. 63.

Choudhary et al., Angew. Chem. Int. Ed. 2005, 44, 4381-4385.

J.R. Aderson, Appl. Catal. 47, (1989) 177.

J.S. Lee et al, Catal. Rev-Sci. Eng., 30 (1988) 249.

G.J. Hutchings et al., Chem Soc.Rev., 18 (1989) 25.

Science 153 (1966) 1393 "High Temperature Synthesis of Aromatics Hydrocarbons from Methane".

J.H. Lunsford, Ang Chem. Intl. Ed. Engl. 24 (1995), 970.

J. Haggin, Methane to Gasoline Plant Adds to New Zealand Liquid Fuel Resources, Chemical & Engineering News p. 22, Jun. 22, 1987.

J.H. Lunsford, The Catalytic Conversion of Methane to Higher Hydrocarbons, Catal. Today, vol. 6, p. 235, 1990.

Synthesis gas conversion utilizing mixed catalyst composed of CO reducing catalyst and solid acid: II. Direct syntheseis of aromatic hydrocarbons from synthesis gas. Kaoru Fujimoto, Yoshihiro Kudo, Hiro-o Tominaga. May 1984, Journal of Catalysis, vol. 87, is. 1, 136-143.

Selective Conversion of Methanol into Aromatic Hydrocarbons Over Silver Exchanged ZAM-5 Zeolites. Inoue, Yoshihiro, Nakashiro, Katsumi, Ono, Yoshio. S.L.: Elsevier; 1995, Microporous Materials, vol. 4, 379-383.

Sachchit Majhi et al. "Direct conversion of methane with methanol toward higher hydrocarbon over GA modified Mo/H-ZSM-5 catalyst", Journal of Industrial and Engineering Chemistry, vol. 20, No. 4, Oct. 14, 2013, pp. 2364-2369.

Anunziata O.A. et al: "Methane transformation into aromatic hydrocarbons by activiation with LPG over Zn-ZSM-11 Zeolite" Catalysis Letters, Springer New York LLC, United States, vol. 58, No. 4, Apr. 1, 1999, pp. 235-239.

Zhang, C-L et al: "Aromatization of Methane in the absence of oxygen over mo-based catalysts supported on different types of zeolites", Catalysis Letters, vol. 56, No. 4, Jan. 1 1999, 207-213.

Parisa Moghimpour Bijani et al: "nonoxidative Aromatization of $CH_4$ using $C_3H_8$ as a Coreactant: Thermodynamic and Experimental Analysis", Industrial and Engineering Chemistry Research, vol. 53, No. 2, Jan. 15, 2014, pp. 572-581.

* cited by examiner

PRODUCTION OF $C_{2+}$ OLEFINS

CROSS REFERENCE TO RELATED APPLICATIONS

This application claims priority to U.S. Patent Application Ser. No. 61/912,886, filed Dec. 6, 2013, the disclosure of which is incorporated herein by reference in its entirety. This application also claims priority to European Patent Application No. EP 14153944.5, filed Feb. 5, 2014. Cross reference is made to the following related patent applications: (i) P.C.T. Patent Application No. PCT/US2014/065947, filed Nov. 17, 2014; (ii) U.S. patent application Ser. No. 14/543,271, filed Nov. 17, 2014; (iii) P.C.T. Patent Application No. PCT/US2014/065956, filed Nov. 17, 2014; (iv) U.S. patent application Ser. No. 14/543,243, filed Nov. 17, 2014; (v) P.C.T. Patent Application No. PCT/US2014/065969, filed Nov. 17, 2014; (vi) U.S. patent application Ser. No. 14/543,426, filed Nov. 17, 2014; (vii) P.C.T. Patent Application No. PCT/US2014/065961, filed Nov. 17, 2014; and (viii) U.S. patent application Ser. No. 14/543,405, filed Nov. 17, 2014.

FIELD

This disclosure relates to the production of $C_{2+}$ olefins from feeds containing methane and at least one co-reactant, to materials and equipment useful in such processes, and to the use of such olefins in, for example, the production of polymers.

BACKGROUND

Although methane is abundant, its relative inertness has limited its utility in conversion processes for producing higher-value hydrocarbons. For example, oxidative coupling methods generally involve highly exothermic and potentially hazardous methane combustion reactions frequently require expensive oxygen generation facilities and produce large quantities of environmentally sensitive carbon oxides. Non-oxidative methane conversion is equilibrium-limited, and temperatures ≥ about 800° C. are needed for methane conversions greater than a few percent.

Catalytic processes have been proposed to co-convert methane and ethylene to higher hydrocarbons. For example, a process disclosed in *Heterocyclic Dissociation of C—H Bond of Methane over $Ag^+$-exchanged Zeolites and Conversion of Methane into Higher Hydrocarbons in the Presence of Ethene or Benzene*, T. Baba and K. Inazu, Chemistry Letters, 35 (2), 142-147, 2006, involves the heterocyclic dissociation of methane over silver cationic clusters in $Ag^+$-exchanged zeolites in the presence of an ethylene co-feed. The dissociation leads to the formation of silver hydride and methyl cations, which react with the ethylene co-feed to produce propylene.

Since ethylene is itself a valuable hydrocarbon, processes are desired which produce higher molecular weight unsaturated hydrocarbons from methane without the need for unsaturated co-reactants, such as ethylene. It would also be beneficial if such processes did not produce large amounts of low-value saturated hydrocarbon (e.g., ethane) and could be operated such that the relative amounts of $C_2$ unsaturates and $C_3$ unsaturates in the product are adjustable.

SUMMARY

The invention relates to the production of $C_{2+}$ olefin, particularly ethylene and propylene, from feeds containing methane and other hydrocarbons. It has been found that by contacting a feed containing methane and one or more of (i) $C_{2+}$ alkane, (ii) syngas, and (iii) alcohol, with at least one molecular sieve, high conversion to $C_{2+}$ olefin is achieved at relatively low reaction temperatures (e.g., temperatures ≤700° C.). In addition, it has been found that utilizing relatively high space velocities favor the production of olefins rather than aromatics. The molecular sieve can comprise, e.g., at least one small pore zeolite, such as zeolite having a geometric mean of the cross-sectional dimensions of the pores ≤5.3 Å.

It is observed that when a feed comprising methane and the specified co-reactant reacts in the presence of at least one small-pore molecular sieve catalyst, the reaction's product includes (i) at least 5 wt. % of $C_{2+}$ olefin, based on the weight of the product, and (ii) molecular hydrogen.

In one aspect, the invention relates to a process for producing $C_{2+}$ olefin from a feed comprising at least 9 mole % of methane and at least 4% of the specified co-reactant, the mole percents being per mole of the feed. The process includes contacting the feed with a catalyst comprising at least one molecular sieve, the molecular sieve comprising at least one set of pores of substantially uniform size extending through the molecular sieve, wherein geometric mean of the cross-sectional dimensions of each of the pores is less than or equal to 5.3 Å. The contacting conditions can include, e.g., exposing the catalyst and feed to a temperature ≤700° C., to convert at least part of the methane and co-reactant in the feed to a product comprising $C_{2+}$ olefin. The process further includes separating at least part of the $C_{2+}$ olefin from the product, e.g., for storage and/or further processing. Non-limiting examples of suitable molecular sieves include those selected from the group consisting of CHA, AEL, AEI, LEV, AFX, ERI, TON, MTT, FER, MFS, and MWW framework type molecular sieves and mixtures thereof.

The co-reactant optionally comprises ethane and/or propane, for example, such that the feed comprises from 40 mole % to 95 mole % methane and from 5 mole % to 60 mole % ethane and/or propane; the mole percents being per mole of the feed. The feed may be derived from natural gas. The contacting conditions can optionally include a feed gas hourly space velocity of at least 200 $cm^3$/h/g of catalyst, such as at least 2000 $cm^3$/h/g of catalyst, for example at least 4000 $cm^3$/h/g of catalyst.

DETAILED DESCRIPTION

Definitions

For the purpose of this description and appended claims, the following terms are defined. The term "$C_n$" hydrocarbon wherein n is a positive integer, e.g., 1, 2, 3, 4, or 5, means a hydrocarbon having n number of carbon atom(s) per molecule. The term "$C_{n+}$" hydrocarbon wherein n is a positive integer, e.g., 1, 2, 3, 4, or 5, means hydrocarbon having at least n number of carbon atom(s) per molecule. The term "hydrocarbon" encompasses mixtures of hydrocarbon having different values of n. For example, the term $C_{1+}$ hydrocarbon encompasses methane and ethane. The term "$C_{n-}$" hydrocarbon wherein n is a positive integer, e.g., 1, 2, 3, 4, or 5 hydrocarbon having no more than n number of carbon atom(s) per molecule. For example, the term $C_{3-}$ hydrocarbon encompasses methane, ethane, and propane. The term "syngas" means a mixture comprising at least 12.0 mole % of molecular hydrogen and at least 0.4 mole % of carbon monoxide, per mole of the mixture.

As used herein, the numbering scheme for the groups of the Periodic Table of the Elements is as disclosed in Chemical and Engineering News, 63(5), 27 (1985).

Direct Conversion of Methane to Olefins

In certain aspects, the invention relates to a process for catalytically producing olefins from a feed comprising methane and at least one co-reactant. The co-reactant can comprise one or more of $C_{2+}$ alkane, syngas and alcohol. Examples of certain feeds will now be described in more detail. The invention is not limited to the use of such feeds, and this description is not meant to foreclose the use of other feeds within the broader scope of the invention.

The process can employ a feed that is primarily in the vapor phase. For example, the feed can comprise of at least 9 vol. %, such as at least 25 vol. %, for example, at least 40 vol. %, and, in some aspects up to 96 vol. % of methane, and at least 4 vol. %, such as at least 10 vol. %, of co-reactant, the volume percents being based on the volume of the feed. Optionally, the feed has a molar ratio of methane to co-reactant in the range of from 0.1:1 to 20:1, such as from 1:1 to 15:1, for example, from 2:1 to 7:1.

Optionally, the feed further comprises ≥0.1 vol. % diluent, based on the volume of feed. Diluent generally comprises species which do not react in significant amounts with the methane or co-reactant under the specified operating conditions. Suitable diluent includes one or more of molecular hydrogen, carbon dioxide, hydrogen sulfide, and molecular nitrogen. In certain aspects, the feed comprises diluent in an amount in the range of from 0.1 vol. % to 50 vol. %, based on the volume of feed. Where present, some or all of the diluent can be present as by-products of the process used to produce the feed's methane and/or co-reactant, e.g., as by-products of a natural gas purification stage.

$C_{2+}$ Alkane Co-Reactant

In certain aspects, the co-reactant comprises $C_{2+}$ alkanes, e.g., ≥90.0 mole % of $C_{2+}$ alkanes, per mole of the co-reactant, such as ≥99.0 mole %. Examples of suitable $C_{2+}$ alkanes include those having a critical diameter less than that of benzene. The $C_{2+}$ alkane can comprise ≥31 mole % of a mixture of ethane and propane, per mole of the $C_{2+}$ alkane, e.g., ≥57 mole %, such as ≥80 mole %, or ≥98 mole %. Optionally, the $C_{2+}$ alkane comprises (i) ≥35 mole % of ethane, e.g., ≥62 mole %, such as ≥83 mole %, or ≥98 mole %; or (ii) ≥27 mole % of propane, e.g., ≥52 mole %, such as ≥77 mole %, or ≥97 mole %; the mole percents being based per mole of the $C_{2+}$ alkane. In certain aspects, the feed is in the vapor phase and comprises from 40 vol. % to 95 vol. %, such as 60 vol. % to 90 vol. % methane, and 5 vol. % to 60 vol. % $C_{3-}$ alkane, such as from 10 vol. % to 40 vol. % of a mixture of ethane and propane. The volume percents being per volume of feed.

While not wishing to be bound by any theory or model, it is believe that when the co-reactant includes propane, a representative reaction between methane and propane to form $C_{2+}$ olefins is as follows:

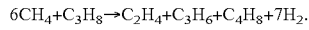

$6CH_4+C_3H_8 \rightarrow C_2H_4+C_3H_6+C_4H_8+7H_2$.

Suitable feeds comprising $C_{2+}$ alkanes as a co-reactant can be derived from natural gas. Raw natural gas recovered at a well head usually contains impurities and contaminants including water vapor, hydrogen sulfide, carbon dioxide, nitrogen, and other compounds. It is generally desirable to purify the raw gas before deriving the feed (e.g., the methane and/or co-reactant). Purification can be carried out by any convenient method, including one or more of hydrogenation, dehydrogenation, sulfur, and acid gas removal techniques. Desired feed components, e.g., methane and/or co-reactant, can then be separated from the purified natural gas by any convenient separation, e.g., conventional separation methods such as fractionation. Optionally, the feed is derived from a purified natural gas, which contains impurities such as nitrogen compounds, sulfur compounds and carbon oxides in an aggregate amount that is ≤1.0 wt. %, based on the weight of the purified natural gas, e.g., ≤0.1 wt. %. Optionally, the natural gas is wet natural gas. Besides methane, wet natural gas contains a significant amount of $C_2$ to $C_5$ alkane, which provides a convenient source of methane and co-reactant, generally within the specified methane:co-reactant molar ratio for the feed without the need for adjusting the relative amounts of these molecules in the natural gas before deriving the feed.

Aspects of deriving the feed from natural gas will now be described in more detail. The invention is not limited to these aspects, and this description is not meant to foreclose other aspects for deriving the feed within the broader scope of the invention.

Oil and gas can be obtained from a well reservoir, which includes trapped oil and gas within rock formations. One form of an oil and gas well reservoir includes at least one subsurface pool of hydrocarbons contained in porous sedimentary rock. A layer of impermeable rock formations, termed cap rock, generally prevents the escape of the naturally occurring hydrocarbons into overlying sediment and rock formations (the overburden). Various recovery methods may be implemented to extract and recover both the oil and gas hydrocarbons. During recovery, the oil and gas reservoir may produce the crude oil and raw natural gas along with other liquid, gaseous, and solid hydrocarbons.

A hydrocarbon stream can be produced from the reservoir, the hydrocarbon stream generally including natural gas, oil, water, and combinations thereof. The hydrocarbon stream can be flowed into a gas-oil separator for separating from the hydrocarbon stream at least one raw natural gas stream, at least one oil stream, and optionally streams comprising one or more of other liquids. The raw natural gas can be further processed in one or more purification stages, to produce a purified natural gas. By-products from the purification stage, e.g., one or more of sulfur compounds, including one or more of hydrogen sulfide mercaptans, sulfides, and other organosulfur compounds, water, trace metals, and entrained liquids and solids, can be conducted away.

Syngas Co-Reactant

In certain aspects the co-reactant comprises syngas e.g., ≥97 mole % of syngas, based on per mole of the co-reactant, such as ≥99 mole %. The syngas can comprise, e.g., molecular hydrogen and ≥0.4 mole % of carbon monoxide, based on per mole of the syngas, and the syngas can have an $H_2$:$(CO+CO_2)$ molar ratio in the range of from 0.5 to 20, such as an $H_2$:CO molar ratio in the range of from 0.5 to 20, or 0.6 to 10, or 0.8 to 4. The syngas can be produced, e.g., from methane and/or other carbon-containing source material. The type of carbon-containing source material used is not critical. The source material can comprise, e.g., methane and other lower ($C_{4-}$) alkanes, such as contained in a natural gas stream, or heavier hydrocarbonaceous materials, such as coal and biomass. Desirably, the source material comprises ≥10 vol. %, such as ≥50 vol. %, based on the volume of the source material, of at least one hydrocarbon, especially methane.

The source material can be converted to syngas by any convenient method, including those well-established in the art. Suitable methods include those described in U.S. Patent Application Publication Nos. 2007/0259972 A1, 2008/0033218 A1, and 2005/0107481 A1, each of which is incorporated by reference herein in its entirety.

For example, natural gas can be converted to syngas by steam reforming. The first step normally involves the removal of inert components in the natural gas, such as nitrogen, argon, and carbon dioxide. Natural gas liquids can also be recovered and directed to other processing or transport. The purified natural gas is then contacted with steam in the presence of a catalyst, such as one or more metals or compounds thereof selected from Groups 7 to 10 of the Periodic Table of the Elements supported on an attrition resistant refractory support, such as alumina. The contacting is normally conducted at high temperature, such as in the range of from 800° C. to 1100° C., and pressures ≤5000 kPa. Under these conditions, methane converts to carbon monoxide and hydrogen according to reactions, such as:

$$CH_4+H_2O=CO+3H_2.$$

Steam reforming is energy intensive in that the process consumes over 200 kJ/mole of methane consumed. A second method is partial oxidation, in which the methane is burned in an oxygen-lean environment. The methane is partially-oxidized to carbon monoxide (reaction (i)), with a portion of the carbon monoxide being exposed to steam reforming conditions (reaction (ii)) to produce molecular hydrogen and carbon dioxide, according to the following representative reactions:

$$CH_4+3/2O_2=CO+2H_2O \qquad (i),$$

$$CO+H_2O+H_2O=CO_2+H_2 \qquad (ii).$$

Partial oxidation is exothermic and yields a significant amount of heat. Because one reaction is endothermic and the other is exothermic, steam reforming and partial oxidation is often performed together for efficient energy usage. Combining the steam reforming and partial oxidation yields a third process wherein the heat generated by the partial oxidation is used to drive the steam reforming to yield syngas.

In certain embodiments, the co-reactant comprises alcohol, e.g., $C_{1+}$ alcohol, such as methanol. For example, the co-reactant can comprise ≥90.0 wt. % alcohol, based on the weight of the co-reactant, e.g., 99.0 wt. %.

Alcohol co-reactant can be produced from syngas, for example. In certain aspects, syngas cis catalytically converted to alcohol, e.g., $C_{1+}$ alcohol, such as methanol. Conventional alcohol synthesis processes can be used, but the invention is not limited thereto. In one aspect, the conversion of syngas to methanol is carried out at very high selectivities using a mixture of copper, zinc oxide, and alumina at a temperature of 200° C. to 400° C. and pressures of 50-500 atm. In addition to $Cu/ZnO/Al_2O_3$, other catalyst systems suitable for methanol synthesis include $Zn(VCr_2O_3$, $Cu/ZnO$, $Cu/ZnO/Cr_2O_3$, $Cu/ThO_2$, $Co/S$, $Mo/S$, $Co/Mo/S$, $Ni/S$, $Ni/Mo/S$, and $Ni/Co/Mo/S$. The alcohol synthesis can be carried out separately from (e.g., upstream of) the specified conversion of methane to $C_{2+}$ olefin, but this is not required. In certain aspects, methanol synthesis is carried out substantially simultaneously with the specified conversion of methane to $C_{2+}$ olefin, e.g., by (i) utilizing syngas as a co-reactant and (ii) including at least one alcohol-synthesis functionality in the specified $C_{2+}$ olefin synthesis catalyst.

Combined Co-Reactant

In certain aspects, the co-reactant comprises $C_{2+}$ alkane and alcohol, e.g., ≥7 mole % of $C_{2+}$ alkane and ≥64 mole % of methanol, the mole percents being based on per mole of the co-reactant. Example, the co-reactant can comprise a mixture of $C_{2+}$ alkane and methanol, the mixture having a $C_{2+}$ alkane:methanol weight ratio of 0.1 to 10.0, e.g., in the range of 0.5 to 5.0.

Molecular Sieve Catalyst for $C_{2+}$ Olefin Synthesis

The reaction of the methane with the specified co-reactant to produce $C_{2+}$ olefin is conducted in the presence of a catalyst comprising at least one small pore molecular sieve. Certain representative molecular sieves will now be described in more detail. The invention is not limited to these molecular sieves, and this description is not meant to foreclose the use of other molecular sieves within the broader scope of the invention.

In certain aspects, the small pore molecular sieve include those having at least one set of pores of substantially uniform size extending through the molecular sieve, wherein geometric mean of the cross-sectional dimensions of each of the pores is less than or equal to 5.3 Å. Examples of suitable molecular sieves include those having the framework types CHA, AEL, AEI, LEV, AFX, ERI, TON, MTT, FER, MFS, and MWW (see "Atlas of Zeolite Framework Types", eds. Ch. Baerlocher, L. B. McCusker, D. H. Olson, Elsevier, Sixth Revised Edition, 2007, which is hereby incorporated by reference). For example, MWW framework type molecular sieves have two sets of pores, each defined by 10-ring channels, extending through the molecular sieve, wherein the pores of one set having cross-sectional dimensions of 5.5 Å×4.0 Å (geometric mean 4.7 Å) and the pores of the other set having cross-sectional dimensions of 5.1 Å×4.1 Å (geometric mean 4.6 Å). Thus, the geometric mean of the cross-sectional dimensions of all the pores defined by these 10-ring channels in MWW zeolites is less than or equal to 5.3 Å. The large (7.1 Å diameter) surface pockets of MWW zeolite are not pores extending through the molecular sieve and so are not considered in this calculation. Other molecular sieves that can be used in the present process for converting methane and $C_{2+}$ alkanes to $C_{2+}$ olefins include those having the framework types CHI, LOV, NAB, NAT, RSN, STT, and VSV.

Aluminosilicate molecular sieves are within the scope of the invention. Examples of suitable aluminosilicate molecular sieves include ZSM-22 (described in U.S. Pat. No. 4,556,477), ZSM-23 (described in U.S. Pat. No. 4,076,842), ZSM-35 (described in U.S. Pat. No. 4,016,245), ZSM-57 (described in U.S. Pat. No. 4,873,067), MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO 97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof.

Silicoaluminophosphate molecular sieve is also within the scope of the invention. Examples of suitable silicoaluminophosphate molecular sieve include SAPO-34 (described in U.S. Pat. No. 4,440,871), SAPO-11 (described in U.S. Pat. No. 4,440,871), SAPO-17 (described in U.S. Pat. No. 4,440,871), SAPO-18 (described by Chen et al in *Catalysis Letters,* 28, 241-248 (1994)), SAPO-35 (described in U.S. Pat. No. 4,440,871), SAPO-56 (described in U.S. Pat. No. 5,370,851) and mixtures thereof. Mixtures of aluminosilicates and silicoaluminophosphates may also be employed.

The catalyst employed to convert the methane/co-reactant mixture to $C_{2+}$ olefin generally further comprises at least 0.1 wt. %, such as from 0.1 to 5 wt. %, of at least one dehydrogenation component. The dehydrogenation component may comprise (i) one or more neutral metals selected from Ag, Mo, Zn, La, Re, Co, Cu, W, Fe, Ni, Pt, Pd, In, and Ga and/or one or more oxides, sulfides and/or carbides of these metals. The dehydrogenation component can be provided on the catalyst by any convenient method, including conventional methods. For example, the dehydrogenation component can be provided on the catalyst by impregnation of the molecular sieve with a solution of a compound of the relevant metal, followed by conversion of the metal compound to the desired form, namely neutral metal, oxide, sulfide and/or carbide.

Molecular sieve composites are within the scope of the invention. For example, the molecular sieve can be composited with another material which is resistant to the temperatures and other conditions employed in the conversion reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. For example, the relative proportions of molecular sieve and inorganic oxide can be in the range of from about 1 to about 90 percent by weight, typically, in the range of about 2 to about 80 wt. % of the composite—particularly when the composite is prepared in the form of beads.

The feed and catalyst are exposed to reaction conditions effective for converting the feed's methane and co-reactant to $C_{2+}$ olefin. Representative reaction conditions will now be described in more detail. The invention is not limited to these reaction conditions, and this description is not meant to foreclose other reaction conditions within the broader scope of the invention.

In certain aspects, a feed comprising methane and co-reactant is reacted in the presence of the specified catalyst to produce $C_{2+}$ olefins, where the reaction conditions include one or more of (i) exposing the methane and co-reactant to a temperature of no more than 700° C., such as in the range of from 400° C. to 700° C., (ii) at a pressure in the range of from 1 bar (absolute) to 5 bar (absolute) (100 to 500 kPa absolute), and (iii) gas hourly space velocity ≥200 cm$^3$/h/g of catalyst, such as ≥2000 cm$^3$/h/g of catalyst, for example ≥4000 cm$^3$/h/g of catalyst. For example, the reaction conditions include (i) exposing the methane and co-reactant to a temperature in the range of from 450° C. to 650° C., (ii) a pressure in the range of from 2 bar (absolute) to 4 bar (absolute) (200 to 400 kPa absolute), and (iii) gas hourly space velocity in the range of from 200 cm$^3$/h/g of catalyst, to 20,000 cm$^3$/h/g of catalyst, e.g., 500 cm$^3$/h/g of catalyst, to 5,000 cm$^3$/h/g of catalyst. When the co-reactant includes ≥86 mole % of syngas, based on per mole of the co-reactant, the molecular sieve preferably includes SAPO-34 and/or Chabazite.

Without wishing to be bound by a theory of operation, it is believed that olefins, which can be precursors for the production of aromatics, will convert into aromatics if allowed to be in contact with the catalyst for longer times. In addition, it is believed that selective production of olefins over aromatics can be favored not only by size selectivity of the molecular sieve catalyst but also by operating at high space velocity. The preferred space velocity range depends on the catalyst, feed and temperature used. Some representative gas hourly space velocities (GHSV) for catalysts operating in the range from 400° C.-700° C. are in the range from 2000-25000 cm$^3$/g/h, preferably 15000-25000 cm$^3$/g/h.

The methane conversion process can be conducted in one or more fixed bed, moving bed or fluidized bed reaction zones. The process can be operated continuously, semi-continuously, or in batch mode.

The methane conversion reaction tends to deposit coke on the catalyst and hence, to maintain the activity of the catalyst, at least part of the catalyst can be continuously or intermittently regenerated. This may be achieved by withdrawing a portion of the catalyst from the or each reaction zone, either on an intermittent, or a continuous basis, and then transferring the catalyst to a separate regeneration zone. In the regeneration zone, the coked catalyst may be contacted with a hydrogen-containing gas under conditions effective to convert at least a portion of the carbonaceous material on the catalyst to methane, which can then be recycled back to the conversion reaction. In one embodiment, the hydrogen required for the regeneration is obtained at least in part from the hydrogen-containing effluent from the methane conversion reaction.

Depending on the conditions and catalyst employed, at least 1%, such as from 5% to 50%, of the methane in the feed (on a weight basis) is converted to a product mixture comprising $C_{2+}$ olefin. Generally, the molar ratio of olefins to aromatics in the product mixture is greater than 0.5:1, more preferably greater than 1:1, more preferably greater than 10:1. The distribution of light olefins in the $C_{2+}$ unsaturated product depends on operating conditions, the pore size and acid activity of the molecular sieve, with SAPO-34 and SAPO-56 tending to produce the highest selectivity to ethylene and propylene.

The $C_{2+}$ olefin can readily be removed from the other conversion products, such as hydrogen, and any residual methane and co-reactant by any convenient method, e.g., by conventional separation methods.

The $C_{2+}$ olefin produced by the present process can be used as feedstock in a variety of important industrial processes, including the production of homopolymers and copolymers of ethylene and propylene.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated, and are expressly within the scope of the invention. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group consisting of," or "is" preceding the recitation of the composition, component, or components, and vice versa.

The invention claimed is:

1. A process for producing one or more of $C_{2+}$ olefin, the process comprising:
    (a) providing a feed comprising at least 9 vol. % of methane and at least 4 vol. % of at least one co-reactant selected from the group consisting of $C_{2+}$ alkane, syngas, and alcohol;
    (b) providing a catalyst comprising at least one molecular sieve, the molecular sieve having a framework of AFX, ERI, CHI, LOV, NAB, NAT, RSN, STT, VSV, or mixtures thereof;
    (c) contacting the feed with the catalyst under conditions, including a temperature of no more than 700° C., effective to convert at least part of the methane and co-reactant in the feed to a product comprising at least one $C_{2+}$ olefin, wherein from 5 wt. % to 50 wt. % of the methane in the feed is converted; and
    (d) separating at least part of the at least one $C_{2+}$ olefin from the product.

2. A process for producing $C_{2+}$ olefin, the process comprising:
    (a) providing a feed comprising at least 9 vol. % of methane and at least 4 vol. % of at least one co-reactant selected from the group consisting of $C_{2+}$ alkane, syngas, and alcohol;
    (b) providing a catalyst comprising at least one molecular sieve selected from the group consisting of CHI, LOV, NAB, NAT, RSN, STT, VSV, and mixtures thereof;
    (c) contacting the feed with the catalyst under conditions, including a temperature of no more than 700° C., effective to convert at least part of the methane and co-reactant in the feed to a product comprising at least one $C_{2+}$ olefin, wherein from 5 wt. % to 50 wt. % of the methane in the feed is converted; and
    (d) separating at least part of the at least one $C_{2+}$ olefin from the product.

3. The process of claim 2, wherein the catalyst comprises at least 0.1 wt % of at least one dehydrogenation component based on the weight of the catalyst.

4. The process of claim 3, wherein the dehydrogenation component comprises (i) one or more neutral metals, (ii) one or more metal oxides, (iii) one or more metal sulfides and/or (iv) one or more metal carbides.

5. The process of claim 4, wherein the hydrogenation metal comprises at least one metal selected from the group consisting of Ag, Mo, Zn, Re, Cu, La, Co, W, Fe, Ni, Pt, Pd, In, and Ga.

6. The process of claim 2, wherein a molar ratio of methane to co-reactant in the feed is from 0.1:1 to 20:1.

7. The process of claim 6, wherein the molar ratio of methane to co-reactant in the feed is in the range of from 1:1 to 15:1.

8. The process of claim 6, wherein the molar ratio of methane to co-reactant in the feed is in the range of from 2:1 to 7:1.

9. The process of claim 2, wherein the feed is derived from natural gas.

10. The process of claim 2, wherein the conditions in (c) include a temperature in a range of from 400° C. to 700° C. and a pressure from 1 bar (absolute) to 5 bar (absolute).

11. The process of claim 2, wherein the conditions in (c) include a gas hourly space velocity of at least 200 cm$^3$/h/g of catalyst.

12. The process of claim 2, wherein a molar ratio of olefins to aromatics in the product is greater than 0.5:1.

13. The process of claim 2, wherein the at least one co-reactant comprises 98 mole % of $C_{2+}$ alkane, based on per mole of the at least one co-reactant.

14. The process of claim 2, wherein the feed comprises from 40 vol. % to 95 vol. % methane and from 5 vol. % to 60 vol. % ethane and/or propane.

15. The process of claim 2, wherein the at least one co-reactant comprises 99.0 vol. % of alcohol, based on a total volume of the at least one co-reactant.

16. The process of claim 15, wherein the alcohol is produced from syngas.

17. The process of claim 2, further comprising polymerizing the at least one $C_{2+}$ olefin separated in step (d) to produce a polyolefin.

18. The process of claim 2, wherein the at least one $C_{2+}$ olefin includes ethylene and propylene.

19. The process of claim 18, further comprising polymerizing at least a portion of the ethylene and/or at least a portion of the propylene.

* * * * *